(12) United States Patent
Kheradvar et al.

(10) Patent No.: US 7,780,724 B2
(45) Date of Patent: *Aug. 24, 2010

(54) MONOLITHIC IN SITU FORMING VALVE SYSTEM

(75) Inventors: Arash Kheradvar, Blythewood, SC (US); Morteza Gharib, San Marino, CA (US)

(73) Assignee: California Institute of Technology, Pasadena, CA (US)

(*) Notice: Subject to any disclaimer, the term of this patent is extended or adjusted under 35 U.S.C. 154(b) by 12 days.

This patent is subject to a terminal disclaimer.

(21) Appl. No.: 12/011,996

(22) Filed: Jan. 29, 2008

(65) Prior Publication Data

US 2008/0161909 A1 Jul. 3, 2008

Related U.S. Application Data

(63) Continuation-in-part of application No. 11/361,850, filed on Feb. 24, 2006, now Pat. No. 7,331,991.

(60) Provisional application No. 60/898,292, filed on Jan. 30, 2007.

(51) Int. Cl.
*A61F 2/24* (2006.01)

(52) U.S. Cl. ..................................... 623/2.11

(58) Field of Classification Search ............... 623/1.22, 623/2.33, 1.23, 1.24, 1.26, 1.3, 1.15, 1.18, 623/1.19, 1.2, 1.11
See application file for complete search history.

(56) References Cited

U.S. PATENT DOCUMENTS

| | | | |
|---|---|---|---|
| 4,451,936 A | 6/1984 | Carpentier et al. | |
| 4,692,164 A | 9/1987 | Dzemeshkevich et al. | |
| 4,759,758 A | 7/1988 | Gabbay | |
| 4,790,843 A | 12/1988 | Carpentier et al. | |
| 4,851,001 A | 7/1989 | Taheri | |
| 4,994,077 A | 2/1991 | Dobben | |
| 5,032,128 A | 7/1991 | Alonso | |

(Continued)

FOREIGN PATENT DOCUMENTS

EP 0667133 8/1995

(Continued)

OTHER PUBLICATIONS

PCT International Search Report and the Written Opinion of the International Searching Authority.

(Continued)

*Primary Examiner*—David Isabella
*Assistant Examiner*—Jonathan Stroud
(74) *Attorney, Agent, or Firm*—Tope-McKay & Associates (57) ABSTRACT

Described is a monolithic in situ forming valve system. The valve system is delivered in an unformed, collapsed configuration that lacks any functional characteristics commonly associated with a valve before. However, once expanded, the system is transformed into a competent valve for use in a wide variety of applications. The valve system includes a superior expandable structure, an inferior expandable structure, and a helical pre-valve component. The helical pre-valve component comprises a first end attached with the superior expandable structure and a second end attached with the inferior expandable structure. The helical pre-valve component is formed such that expansion of the superior expandable structure and the inferior expandable structure causes the helical pre-valve structure to transform into a functional valve held between each of the expandable structures.

11 Claims, 5 Drawing Sheets

U.S. PATENT DOCUMENTS

| | | | |
|---|---|---|---|
| 5,037,434 | A | 8/1991 | Lane |
| 5,080,668 | A | 1/1992 | Bolz et al. |
| 5,163,953 | A | 11/1992 | Vince |
| 5,282,847 | A | 2/1994 | Trescony et al. |
| 5,332,402 | A | 7/1994 | Teitelbaum |
| 5,360,444 | A | 11/1994 | Kusuhara |
| 5,370,685 | A | 12/1994 | Stevens |
| 5,397,351 | A | 3/1995 | Pavcnik et al. |
| 5,411,552 | A | 5/1995 | Andersen et al. |
| 5,445,626 | A | 8/1995 | Gigante |
| 5,500,014 | A | 3/1996 | Quijano et al. |
| 5,545,214 | A | 8/1996 | Stevens |
| 5,571,175 | A | 11/1996 | Vanney et al. |
| 5,591,195 | A | 1/1997 | Taheri et al. |
| 5,607,464 | A | 3/1997 | Trescony et al. |
| 5,609,626 | A | 3/1997 | Quijano et al. |
| 5,749,890 | A | 5/1998 | Shaknovich |
| 5,824,064 | A | 10/1998 | Taheri |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,925,063 | A | 7/1999 | Khosravi |
| 5,954,766 | A | 9/1999 | Zadno-Azizi et al. |
| 5,957,949 | A * | 9/1999 | Leonhardt et al. .......... 623/1.24 |
| 6,077,298 | A | 6/2000 | Tu et al. |
| 6,106,550 | A | 8/2000 | Magovern et al. |
| 6,106,551 | A | 8/2000 | Crossett et al. |
| 6,132,473 | A | 10/2000 | Williams et al. |
| 6,168,614 | B1 | 1/2001 | Andersen et al. |
| 6,206,911 | B1 | 3/2001 | Milo |
| 6,283,127 | B1 | 9/2001 | Sterman et al. |
| 6,454,799 | B1 | 9/2002 | Schreck |
| 6,458,153 | B1 | 10/2002 | Bailey et al. |
| 6,482,228 | B1 | 11/2002 | Norred |
| 6,530,952 | B2 | 3/2003 | Vesely |
| 6,569,196 | B1 | 5/2003 | Vesely |
| 6,582,462 | B1 | 6/2003 | Andersen et al. |
| 6,638,239 | B1 | 10/2003 | Bergheim et al. |
| 6,652,578 | B2 | 11/2003 | Bailey et al. |
| 6,666,841 | B2 | 12/2003 | Gharib et al. |
| 6,730,118 | B2 | 5/2004 | Spenser et al. |
| 6,736,791 | B1 | 5/2004 | Tu et al. |
| 6,780,164 | B2 | 8/2004 | Bergheim et al. |
| 6,830,584 | B1 | 12/2004 | Seguin |
| 6,830,585 | B1 | 12/2004 | Artof et al. |
| 6,890,350 | B1 | 5/2005 | Walak |
| 6,896,690 | B1 | 5/2005 | Lambrecht et al. |
| 6,908,481 | B2 | 6/2005 | Cribier |
| 6,945,957 | B2 | 9/2005 | Freyman |
| 6,951,571 | B1 | 10/2005 | Srivastava |
| 6,955,656 | B2 | 10/2005 | Bergheim et al. |
| 6,974,476 | B2 | 12/2005 | McGuckin, Jr. et al. |
| 7,007,698 | B2 | 3/2006 | Thornton |
| 7,044,966 | B2 | 5/2006 | Svanidze et al. |
| 7,081,131 | B2 | 7/2006 | Thornton |
| 7,101,396 | B2 | 9/2006 | Artof et al. |
| 2004/0210306 | A1 | 10/2004 | Quijano et al. |
| 2006/0025855 | A1 | 2/2006 | Lashinski et al. |
| 2006/0235511 | A1 | 10/2006 | Osborne |
| 2006/0282157 | A1 | 12/2006 | Hill et al. |

OTHER PUBLICATIONS

PCT International Preliminary Report on Patentability.

* cited by examiner

MONOLITHIC IN SITU FORMING VALVE SYSTEM

PRIORITY CLAIM

The present application is a Continuation-in-Part patent application, claiming the benefit of priority of both U.S. Non-Provisional Utility patent application Ser. No. 11/361,850, filed Feb. 24, 2006, now U.S. Pat. No. 7,331,991 titled, "Implantable Small Percutaneous Valve and Methods of Delivery," and also of U.S. Provisional Patent Application No. 60/898,292, filed Jan. 30, 2007, titled, "Monolithically forming Valve System and its Percutaneous Method of Delivery."

BACKGROUND OF THE INVENTION (1) Technical Field

The present invention is related to a valve system for implantation into a vessel and, more particularly, to a monolithic in situ forming prosthetic valve that is suitable for replacement of a defective valve or a diseased human valve, and methods for delivery thereof.

(2) Background

A variety of valve prostheses, in particular cardiac valve prostheses, have been developed for implantation into the human body. Previously, the large diameter and bulky structure of common prosthetic valves required implementation via open heart surgeries. During the past few years, percutaneous heart valve (PHV) replacement and repair has emerged as an additional therapy to potentially avoid the re-operation in young patients with congenital heart disease or severely sick patients. The challenge for this technology is to develop a collapsible and durable PHV that can be delivered through a reasonably small diameter lumen catheter, non-interfering with the normal anatomy, and being competent without significant valve stenosis.

One such collapsed valve is disclosed in U.S. Pat. No. 5,411,552 to Andersen et al. (the '552 patent), the entire contents of which are incorporated herein by reference. The '552 patent describes a fully formed valve delivered in a collapsed state and expanded in place via the use a balloon. The diameter of the fully formed valve is reduced to the point where it may be delivered in a percutaneous manner and expanded in situ. The device is placed at the desired location by a balloon that is used to expand the stent and the valve. While collapsible and expandable, a device according to the '552 patent is still undesirably large because it includes a pre-formed valve. For example, the device requires 20+French size delivery catheters to deliver the fully formed valve to the target site.

Another fully formed valve which is deliverable via a catheter is disclosed in U.S. Pat. No. 6,582,462 to Andersen et al. (the '462 patent), the entire contents of which are incorporated herein by reference. The '462 patent discloses a fully formed valve prosthesis comprising a collapsible elastic valve mounted on an elastic stent. The commissural points of the elastic collapsible valve are mounted on the cylindrical surface of the elastic stent. A catheter technique permits delivery of the fully formed valve to the target area without the need for surgical intervention in the body. Once at the target site, the collapsed and fully-formed valve and elastic stent are expanded. Once again, the '426 patent describes a fully formed valve. Thus, a disadvantage to this design is the relatively large size of the compressed radial diameter of the fully formed valve when delivered to the target area.

Similarly, U.S. Pat. No. 6,168,614 to Andersen et al. (the '614 patent), the entire contents of which are incorporated herein by reference, discloses a method for endovascularly delivering a fully formed valve through a blood vessel. The '614 patent discloses a variety of steps by which a fully formed tissue valve is attached with a support and delivered to a target site in a collapsed sate. Once in place and expanded, the valve is configured to permit blood flow in one direction and prevent blood flow in an opposite direction. The tissue valve and the support structure are secured to a desired valve location where the support structure and fully formed valve are expanded. As was the case above, a disadvantage to this design is the relatively large size of the compressed radial diameter of the fully formed valve when delivered to the target area.

Another example is U.S. Pat. No. 6,530,952 to Vesely (the '952 patent), the entire contents of which are incorporated herein by reference. The '952 patent discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing whereas a new collapsible valve is then installed, to resume the function of the prosthesis. As was the case above, a drawback to the device of the '952 patent is that, although collapsed, the valve is pre-formed and therefore includes a relatively large, radial diameter.

Yet another example is U.S. Pat. No. 6,569,196 to Vesely (the '196 patent), the entire contents of which are incorporated herein by reference. The '196 patent discloses a system for minimally invasive insertion of a bioprosthetic heart valve. The system includes a collapsible tissue-based valve system, a catheter-based valve delivery system, a surgical platform and a device tracking and visualization system. The collapsible valve system includes a permanent outer frame that is affixed to the patient using conventional sutures or staples and a collapsible valve having a collapsible inner frame that mates with the outer frame. Once again, a drawback to the '196 patent is that it discloses a pre-formed valve.

Another example is U.S. Pat. No. 7,011,681, to Vesely (the '181 patent), the entire contents of which are incorporated herein by reference. The '181 patent discloses cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing. A new collapsible valve is then installed, to resume the function of the prosthesis. Although collapsible, the valve is pre-formed which results in a relatively large radial diameter.

Another example is U.S. Patent Publication No. 2006/0135964, by Vesely (the '964 publication), the entire contents of which are incorporated herein by reference. The '964 publication discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing. A new collapsible valve is then installed, to resume the function of the prosthesis. Once again, the collapsible valve is pre-formed.

Finally, U.S. Patent Publication No. 2006/0136052, by Vesely (the '052 publication), the entire contents of which are incorporated herein by reference, discloses cardiovascular valve assembly comprising a base member that is affixed to a patient using conventional sutures or staples, and a replaceable valve member including a valve frame that supports a plurality of valve leaflets. The valve member mates with the base member, and can be detached from the base member for convenient replacement. As was the case with the references above, the valve is pre-formed and therefore results in a relatively large radial diameter.

Each of the prior art stent valve designs has certain disadvantages. The prior art valve prosthesis generally consists of a support structure with a fully formed tissue valve connected to it. The support structure is typically delivered in a collapsed shape intraluminally and secured to a desired valve location with the support structure in an expanded shape. However, because the valves are delivered in a fully formed, collapsed state, the support structures tend to compressively impinge a portion of the leaflets of the tissue valve at the structure struts when the support structure is expanded by an inflatable balloon. The impinged leaflets tend to deteriorate and calcify, thereby decreasing the life of the valves. Additionally, because they are delivered in a fully formed state, the valves posses a radial diameter that, in some cases, is undesirable.

Thus, a continuing need exists for a deployable, in situ forming valve which has a minimal profile and which does not compressively impinge a portion of the leaflets of the tissue valve upon delivery, thereby decreasing the risk of deterioration and/or calcification.

SUMMARY OF THE INVENTION

As noted above, a need exists for a durable, in situ forming valve. The present invention solves this need by providing a monolithic in situ forming valve system that has a minimal profile and no or minimal tissue impingement concerns during the delivery phase. The monolithic in situ forming valve system is delivered to a target area in a pre-formed, collapsed state lacking the characteristics of a functional valve. The monolithic in situ forming valve system comprises a superior expandable structure, an inferior expandable structure, and a helical pre-valve component placed between the superior and inferior expandable structures while connected to the mentioned superior and inferior components forming a monolithic assembly. The helical pre-valve component comprises a first end attached with the superior expandable structure and a second end attached with the inferior expandable structure. The helical pre-valve component is formed such that expansion of either the superior expandable structure or the inferior expandable structure causes the helical pre-valve structure to transform into a fully functional valve held between each of the expandable structures.

In another aspect, the helical pre-valve component further includes a compliant sheet and at least two appendices attached with the compliant sheet.

In yet another aspect, the expansion of the superior expandable structure and inferior expandable structure causes contraction of the pre-valve component, which causes a first appendix to engage with the inferior expandable structure and a second appendix to engage with the superior expandable structure, thus inducing the compliant sheet to form a valve there between.

In another aspect, the appendices are formed of a shape memory material and form a hook-shape when exposed to a desired temperature.

In yet another aspect, the appendices are configured to secure the pre-valve component to either the superior expandable structure or the inferior expandable structure, thereby fixedly securing the compliant sheet between the superior expandable structure and the inferior expandable structure.

Additionally, the compliant sheet is integrated with a plurality of leaflets made of polymeric materials.

In another aspect, the compliant sheet is formed of a tissue selected from a group consisting of bovine tissue, porcine tissue, and equine pericardial tissue.

Furthermore, the superior expandable structure and inferior expandable structure are at least partially composed of a shape memory material, such that the superior expandable structure and inferior expandable structure have a first compressed memory state shape and second expanded memory state shape, where the superior expandable structure and inferior expandable structure are deliverable in a compressed state and upon expansion, are maintained in the second expanded memory state shape.

Additionally, the superior expandable structure and the inferior expandable structure are in the form of a stent-like crown.

In another aspect, the present invention further comprises a delivery apparatus connected with at least one of the superior expandable structure and the inferior expandable structure.

In yet another aspect, the delivery apparatus further comprises an expansion mechanism configured to selectively expand the superior expandable structure appended over the delivery apparatus and the inferior expandable structure appended over the delivery apparatus. The expansion mechanism is a balloon.

In another aspect, the present invention includes a method for delivering and forming a valve in situ. The method includes an act of providing an in situ forming valve. The in situ forming valve comprises a superior expandable structure; an inferior expandable structure; and a helical pre-valve component. As noted above, the helical pre-valve component includes a first end attached with the superior expandable structure and a second end attached with the inferior expandable structure. The helical pre-valve component is formed such that expansion of the superior expandable structure and the inferior expandable structure causes the helical pre-valve structure to transform into a functional valve held between each of the expandable structures.

In another aspect, the present invention further comprises an act of delivering the in situ forming valve to a target site using a delivery apparatus.

In yet another aspect, the present invention further comprise an act of expanding at least one of the superior expandable structure and the inferior expandable structure, which causes the helical pre-valve structure to vertically shrink and form the functional valve.

Additionally, in the act of providing an in situ forming valve, the helical pre-valve component further comprises a plurality of appendices. The present invention further comprises acts of curling the appendices to form hook-shapes, and hooking the appendices with at least one of the superior expandable structure and the inferior expandable structure.

Finally, in the act of delivering the in situ forming valve, the in situ forming valve is delivered using a procedure selected from a group consisting of a percutaneous procedure, a transapical catheterization, an endoscopic procedure, a laparoscopic procedure, and an open-chest procedure.

BRIEF DESCRIPTION OF THE DRAWINGS

The objects, features and advantages of the present invention will be apparent from the following detailed descriptions of the disclosed aspects of the invention in conjunction with reference to the following drawings, where.

DETAILED DESCRIPTION

The present invention is related to a valve system for implantation into a vessel. More specifically, the present invention is related to an implantable and unformed monolithic valve system that is being formed upon implantation into the vessel (i.e., in situ forming valve). The monolithic in situ forming valve includes a characteristically small profile suitable for replacement of a defective or diseased human valve. The formed valve system can be implanted within a defective valve. The monolithic in situ forming valve includes a superior expandable structure, an inferior expandable structure, and a helical pre-valve component. The helical pre-valve, middle component comprises a first end attached with the superior expandable structure and a second end attached with the inferior expandable structure. The helical pre-valve component is formed such that expansion of the superior expandable structure and the inferior expandable structure causes the helical pre-valve structure to transform into a functional, circular valve held between each of the expandable structures. The circular valve can have a flat or a saddle shape platform.

However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

To assist a reader in understanding the present invention, the monolithic in situ forming valve system will be described first. Second, a method for percutaneous delivering the monolithic in situ forming valve system is described.

(1.0) Monolithic In Situ Forming Valve System

As noted above and as shown in FIG. 1, the present invention is related to a monolithic in situ forming valve system 100 (illustrated in FIG. 1 in a collapsed state). The monolithic in situ forming valve system 100 includes a superior expandable structure 110, an inferior expandable structure 120, and a helical pre-valve component 130. It should be noted that the terms superior and inferior are not used to denote any fixed ordering, but instead are used to denote two distinct structures. It should also be noted that the term "pre valve" component is meant herein to indicate a middle, helical component.

Figure 1:
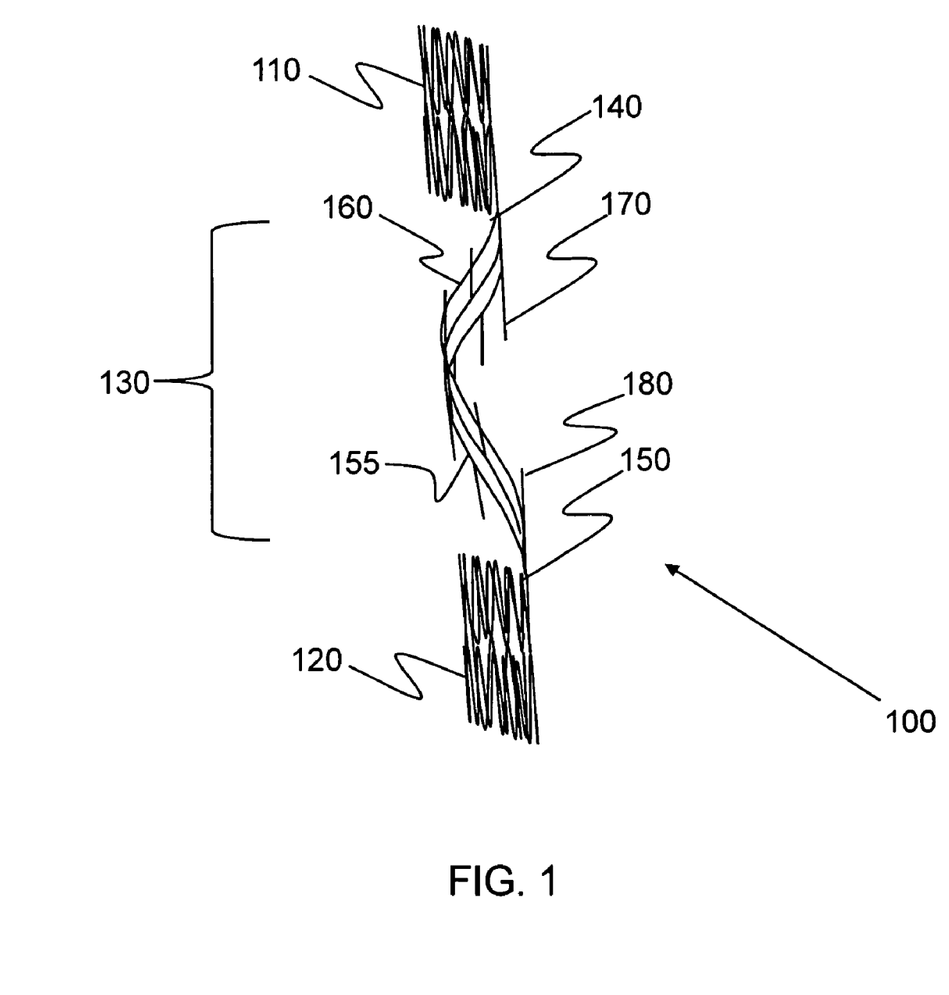
FIG. 1 is an illustration of a monolithic in situ forming valve system in a collapsed state.

In general, the monolithic in situ forming valve system 100 consists of two different configurations, which are reversibly transformable from a first configuration to a second configuration. In a first configuration, the pre-valve component is in a substantially helically collapsed configuration (i.e., initial collapsed configuration) for delivery through a delivery apparatus. Non-limiting examples of suitable delivery apparatus include a catheter, a wire, a guide wire, a flexible tubing, a cannula, or any elongate apparatus with minimal profiles for delivery. Using a suitable delivery apparatus, the monolithic in situ forming valve system 100 can be delivered in its initial collapsed configuration (a pre-valve configuration) through a variety of delivery procedures, non-limiting examples of which include a percutaneous manner, an endoscopic manner, a laparoscopic manner, a trans-apical manner, and the like. The monolithic in situ forming valve system 100 can also be delivered and deployed in an open-chest operation, optionally combined with other surgical procedures.

In the second configuration, the monolithic in situ forming valve system 100 transforms to a functional valvular configuration when the device is deployed. The device can be deployed in any suitable location, non-limiting examples of which include within the lumen of a natural heart valve, cardiac chambers, peripheral/central vessels, a lymphatic vessel, or other body channel, to replace or assist a natural or prosthetic valve. In an alternate embodiment, the monolithic in situ forming valve system 100 may be removable from the implant site by transforming the device from the second, open configuration to the first, collapsed non-functional configuration for retrieval.

The helical pre-valve component 130 comprises a first end 140 attached to the superior expandable structure 110 and a second end 150 attached to the inferior expandable structure 120. The helical pre-valve component 130 is formed such that expansion of the superior expandable structure 110 and/or the inferior expandable structure 120 causes the helical pre-valve structure 130 to transform into a functional valve (illustrated in FIG. 4) securely held between each of the expandable structures 110 and 120, respectively.

As depicted in FIG. 1, the monolithic in situ forming valve system 100 lacks the functional characteristics of a functional valve while in this first, collapsed, pre-valve configuration. The helical pre-valve component 130 may include a variety of secondary structures and may be made from a variety of materials depending upon the particular application. In one aspect, the helical pre-valve component 130 includes a middle helical section 155 and a compliant sheet 160. The compliant sheet 160 at the first end 140 would be attached to or with the second end 150 when the pre-valve is formed to a functional valve, using any suitable connection technique (given the application), a non-limiting example of which includes being sutured.

During the expansion of either the superior expandable structure 110 and/or the inferior expandable structure 120, the pre-valve component 130 (compliant sheet 160 and/or middle helical section 155) shrinks or is otherwise compressed because each of the expandable structures 110 and 120 are moving toward one another. Thus, while expandable structures 110 and 120 expand, the pre-valve component 130 shrinks to bring the folds of the helical structure together and thereby form the functional valve.

Additionally, in another aspect, the present invention can be formed to include at least two appendices (a first appendix 170 and a second appendix 180). The appendices 170 and 180 are made of any suitable material (such as a shape memory material (e.g., Nitinol) or magnetic material) and are attached with the pre-valve component 130 (via the compliant sheet 160 or other suitable attachment).

The appendices 170 and 180 operate as connecting prongs that upon contact with an expandable structure 110 or 120, attach with the expandable structure 110 or 120 to hold the pre-valve component 130 against and between the expandable structure 110 and 120 and affix the superior and inferior expandable structures 110 and 120 together. In other words, the compliant sheet 160 includes several appendices 170 and 180 throughout the compliant sheet 160. As the expandable structures 110 and 120 expand, they inherently expand toward one another. Between the expandable structures 110 and 120 resides the compliant sheet 160 (pre-valve component 130). As the expandable structures 110 and 120 expand, they come into contact with at least one of the appendices 170 and 180. The appendices 170 and 180 are formed such that when they contact one of the expandable structures 110 or 120, the appendices hook around the expandable structure 110 or 120 to affix the compliant sheet 160 there between. For example, the appendices 170 and 180 have super-elastic properties at body temperature and would turn into a hook-shape when they are exposed to a desired temperature. Thus, the hook-shaped appendices 170 and 180 act as a set of sutures that lock the circular formed valve in place and provide a clasp like mechanism for securing the valve within the superior and inferior expandable structures 110 and 120, as well as within the tissue. For example, as the hook-shaped appendices 170 and 180 hook around (curl), they can pass through the surrounding to further affix the device within the appropriate channel or locale. As mentioned above, the appendices 170 and 180 (and other appendices) can be formed of a shape memory material. As another non-limiting example, the appendices 170 and 180 can be formed of a suitably magnetic material such that changing the magnetic field causes the appendices 170 and 180 to form into the hook-shape.

Once the first appendix 170 and the second appendix 180 (there are numerous appendices) are connected with the inferior and superior expandable structures 120 and 110, respectively, a competent (circular bio-prosthetic) valve is formed between the expandable structures 120 and 110. Once formed into the valve, the compliant sheet 160 is positioned such that it operates with a plurality of leaflets, with the leaflets collectively operating as the functional valve.

The superior expandable structure 110 and the inferior expandable structure 120 may be comprised of a wide variety of materials. In one aspect, the superior expandable structure 110 and/or the inferior expandable structure 120 are at least partially composed of a shape memory material. When comprised of a shape memory material, both the superior expandable structure 110 and/or the inferior expandable structure 120 have a first compressed memory state shape (such as the configuration shown in FIG. 1). The superior expandable structure 110 and/or the inferior expandable structure 120 will also include a second, expanded memory state shape such that the superior expandable structure 110 and inferior expandable structure 120 are delivered in a compressed state. Once the shape memory material is activated, the superior expandable structure 110 and/or the inferior expandable structure 120 are formed into their secondary expanded states, thus securing the valve system 100 in place. As another non-limiting example, the expandable structures 110 and 120 can be formed of a suitably magnetic material such that changing the magnetic field causes the expandable structures 110 and 120 to change from the compressed state to the expanded memory state, or vice versa.

It should also be noted that each of the superior expandable structure 110 and the inferior expandable structure 120 can be formed in any suitably expandable and contractible shape. As a non-limiting example, each of the expandable structures 110 and 120 are in the form of a stent-like crown.

The compliant sheet 160 may be made from a single sheet manifold or a compound manifold. Similarly, the dimensions of the compliant sheet 160 may be altered such that the perimeter of the top of the compliant sheet 160 is greater than the bottom of the compliant sheet 160 (or vice versa). The compliant sheet 160 (as either a single sheet manifold or a compound manifold) may be integrated with a plurality of leaflets made of polymeric materials. Alternatively, the compliant sheet 160 may be formed of a tissue selected from a group consisting of bovine tissue, porcine tissue, and equine pericardial tissue.

The monolithic in situ forming valve system 100 may also be manufactured with a delivery apparatus (e.g., catheter). Typically, the superior expandable structure 110 and the inferior expandable structure 120 are appended over the delivery apparatus. In the collapsed state, the superior and the inferior expandable structures 110 and 120 are constricted over the delivery apparatus while interconnected by the pre-valve component 130, which is shaped as the helix/spiral turned over the delivery apparatus.

The delivery apparatus may be configured in a variety of ways in order to expand the collapsed monolithic in situ forming valve system 100. In one embodiment, the superior and inferior expandable structures are made of elastic or expandable materials (such as a spring-like device) that upon releasing a restraint would cause the expandable structures to turn into their expanded configurations. For example, a sheath can be positioned around the expandable structures. In this aspect, upon removal of the sheath, the expandable structures are free to expand as compelled by their inherent properties (for example, a shape memory material may inherently want to expand from a compressed state to an expanded state upon release of a restraint).

In another aspect, the delivery apparatus comprises an expansion mechanism that is configured to selectively expand the superior expandable structure 110 and the inferior expandable structure 120 appended over the delivery apparatus. A non-limiting example of a suitable expansion mechanism of the delivery apparatus is an expandable balloon. For example, the catheter may include a balloon at its tip such that upon reaching the desired location, the balloon is inflated to cause the expandable structures 110 and 120 to expand and thereby form the valve. The balloon can then be deflated with the catheter and attached balloon thereafter removed from the patient's body (leaving the valve in place).

(2.0) Percutaneous Method for Delivering a Monolithic Valve System

Figure 2A:
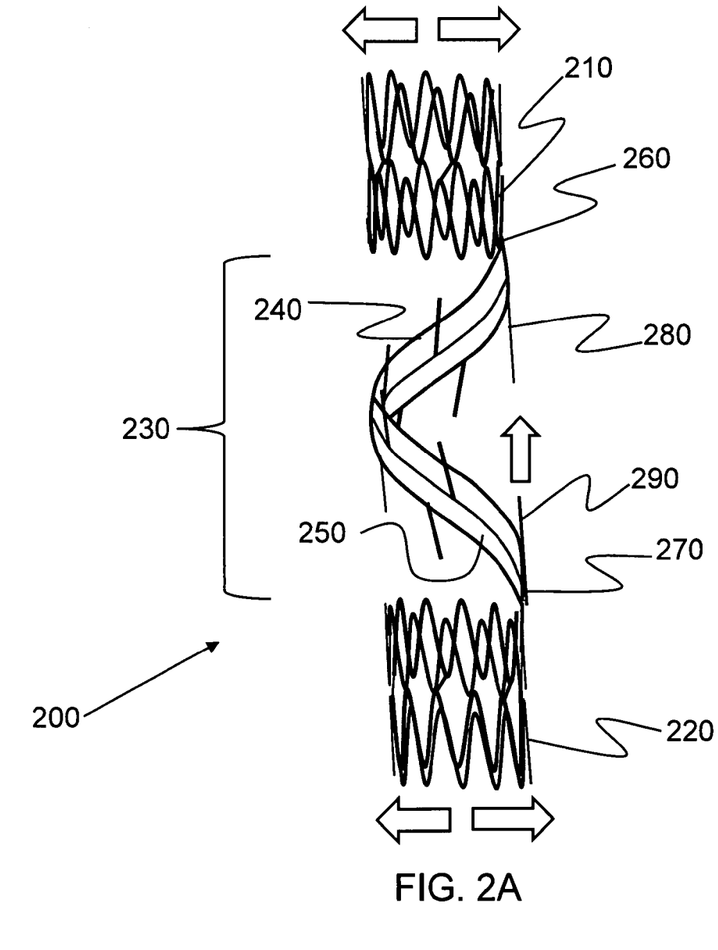
FIG. 2A is the first of two time-sequenced illustrations of a monolithic in situ forming valve system transforming into a fully functional valve; while its superior and inferior components undergo a radial expansion.

As noted above, the present invention also relates to a percutaneous method for delivering the monolithic in situ forming valve system. As shown in FIG. 2A, the method includes the act of providing a monolithic in situ forming valve system 200 that can be expanded upon delivery to a target site. The step of delivering the monolithic system 200 to a target site may be accomplished in a variety of ways, non-limiting examples of which include a percutaneous procedure, a trans-apical catheterization, an endoscopic procedure, a laparoscopic procedure, and an open-chest procedure.

Once delivered to the target site, the monolithic in situ forming valve system is expanded to form the valve and secure it in place. For example, FIG. 2A illustrates the monolithic in situ forming valve system 200 undergoing a radial transformation into a fully functional valve. As shown, the valve system 200 includes a superior expandable structure 210, an inferior expandable structure 220, and a pre-valve component 230 (that includes a compliant sheet 240 and a middle helical section 250). The pre-valve component 230 comprises a first end 260 attached with the superior expandable structure 210 and a second end 270 attached with the inferior expandable structure 220. The compliant sheet 240 is also continuously attached between the first end 260 and the second end 270 and along the middle helical section 250 of the pre-valve component 230. A first appendix 280 and a second appendix 290 are also engaged with the compliant sheet 240.

Figure 2B:
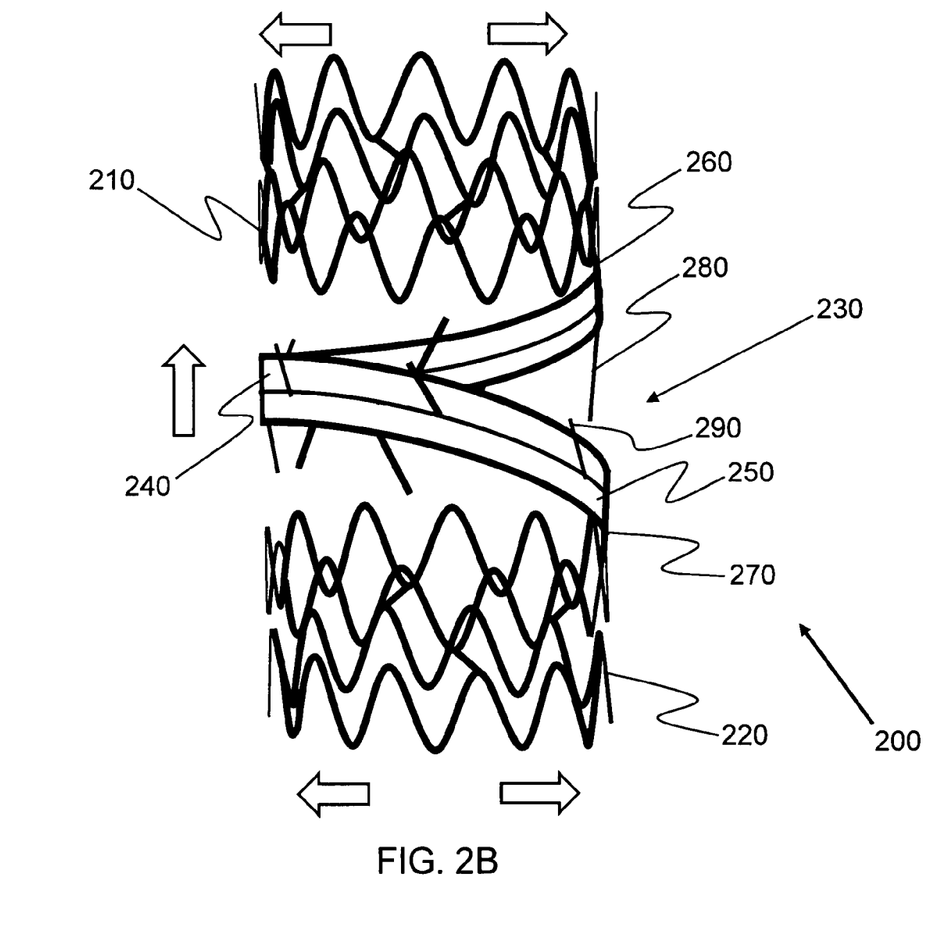
FIG. 2B is the second of two time-sequenced illustrations of a monolithic in situ forming valve system transforming into a fully functional valve; while its superior and inferior components undergo a radial expansion.

Once delivered to the target site, the monolithic system 200 undergoes a progressive expansion process. A slightly expanded state of the monolithic system 200 is illustrated in FIG. 2B. The expansion of either the superior expandable structure 210 and/or the inferior expandable structure 220 induces the contraction in the vertical direction of the pre-valve component 230 between the superior expandable structure 210 and the inferior expandable structure 220. Therefore, the inferior and the superior expandable structures move toward each other. In this intermediate step, the compliant sheet 240 remains continuously attached between the first end 260 and the second end 270. During the process, expansion of the monolithic system 200 induces superior expandable structure 210 to expand towards the inferior expandable structure 220, which causes the helical pre-valve component 230 to shrink and which ultimately causes the appendixes 280 and 290 to engage with the expandable structures 210 and 220. Upon curling of the appendixes 280 and 290 (into the hook-shape), the appendixes 280 and 290 become affixed with at least one of the corresponding expandable structures 210 and 220. In one aspect, the act of expanding the superior expandable structure 210 and inferior expandable structure 220 is aided by the use of an expansion apparatus, such as an inflatable balloon or shape memory material. In another aspect, the expandable structures 210 and 220 can be expanded by elastic recoil of a stent.

As noted above, each of the appendices can turn into a hook-like shape that allows the first appendix 280 to connect with the stent-like crown shape of the inferior expandable structure 220, while the second appendix 290 connects with the superior expandable structure 210, thereby securing the formed valve there between and to the tissue. It should be noted that the present invention can include any suitable number of appendices to connect the expandable structures 210 and 220 with one another and form the valve there between. Finally, once the expansion of the superior expandable structure 210 and the inferior expandable structure 220 is completed, the functional valve is secured in position.

Figure 3:
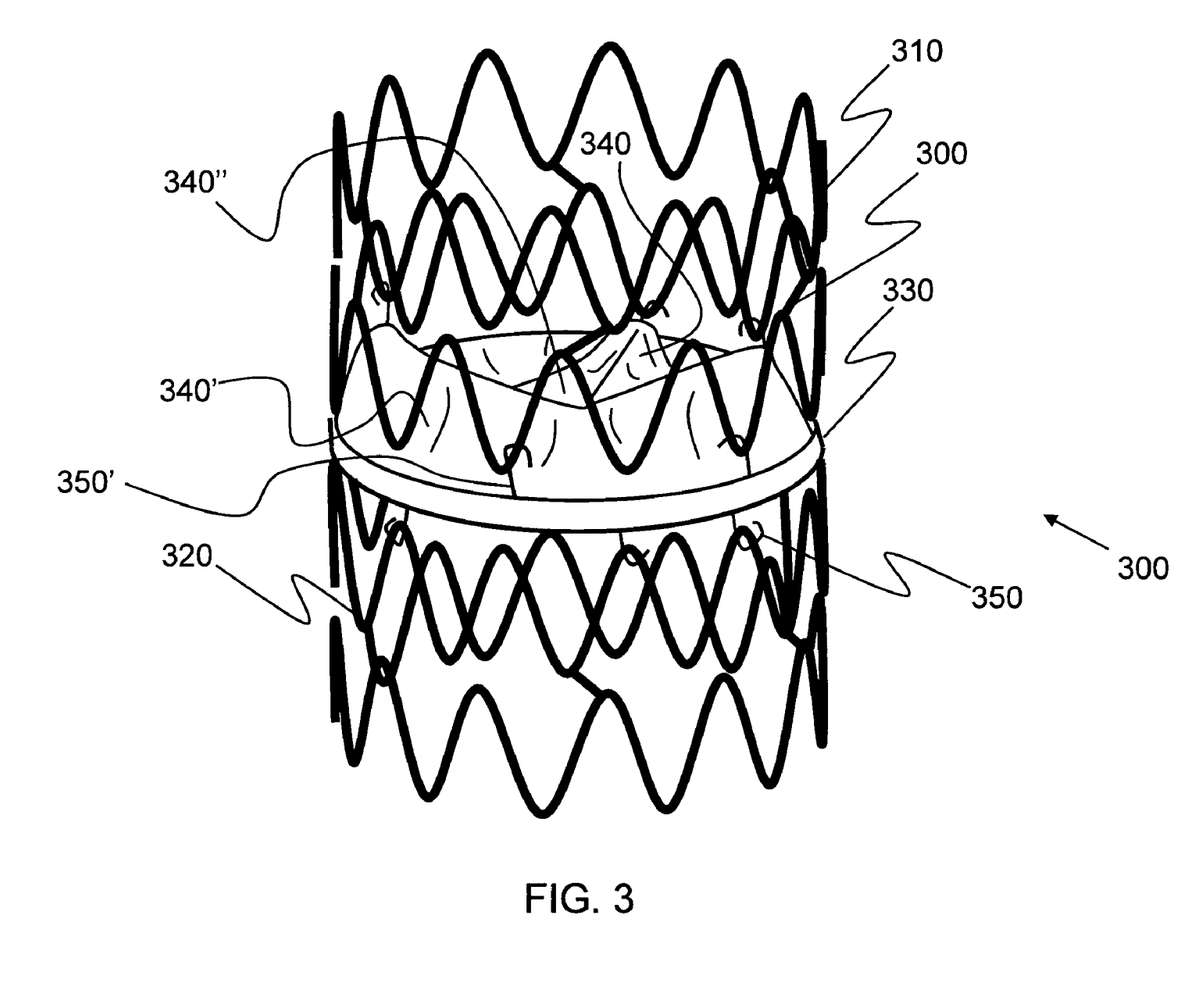
FIG. 3 is an illustration of a fully formed valve according to the present invention.

An example of a fully formed valve 300 is illustrated in FIG. 3. The fully formed valve 300 is shown complete with a superior stent-like crown (i.e., superior expandable structure 310), an inferior stent-like crown (i.e., inferior expandable structure 320), and a three-leaflet valve 330 secured there between. Each of the three-leaflets 340, 340', and 340" are clearly visible. It will be appreciated by one having ordinary skill in the art that the three-leaflet valve 330 may formed with any number of leaflets to suit a particular application.

As shown, the flexible assembly between the superior expandable structure 310 and the inferior expandable structure 320 are fixedly secured to the valve 330 by a network of appendices 350 and 350' (also the middle part is already connected to the superior and inferior structures at both of its ends.). Any suitable number of appendices may be used to form the valve 330. As a non-limiting example, three equally-spaced appendices may be used, separated by 120 degrees from each other. In this example, the valve 330 possesses three operable leaflets.

In another aspect, the pre-valve component includes a specified number of support arms that may be foldable and separated by a specific angle from each other on a circular stent. For example, the support arms are attached with the pre-valve component and assist in the shaping of the leaflets. As another example, three equally-spaced arms separated by 120 degrees from each other can be included such that upon formation of the valve, the support arms help shape the leaflets into a tri-leaflet heart valve.

Figure 4:
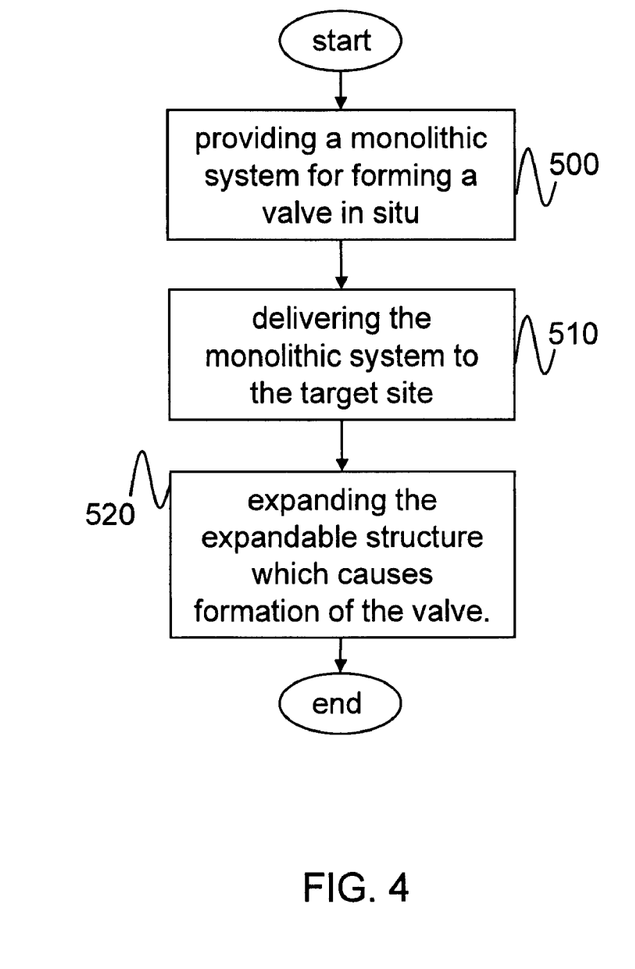
FIG. 4 is a flow diagram reciting the acts of delivering a monolithic system for forming a valve; and Appendix A is a copy of the provisional application to which this application claims priority and provides an additional description of the present invention, entitled, "Monolithic Forming Valve System and its Percutaneous Method of Delivery."

In summary and as shown in FIG. 4, the present invention includes a method for delivering and forming a monolithic, in situ forming valve system. The method begins by providing 500 a monolithic system for forming a valve in situ. A suitable system is generally in a collapsed state and comprises a superior expandable structure, an inferior expandable structure, and helical pre-valve component. While in the compressed state, the monolithic system for forming a valve lacks the functional characteristics of a fully formed valve. The compressed stated of the monolithic system facilitates navigation of the monolithic system through channels for delivery 510 to the target site. Alternatively, the monolithic system may be delivered to the target site via a percutaneous procedure, a trans-apical catheterization, an endoscopic procedure, a laparoscopic procedure, or an open-chest procedure.

Once delivered to the target site, the monolithic system begins the transformation from a first, pre-valve configuration (See FIG. 1) to a functional valve configuration (See FIG. 3). The transformation is initiated by expanding 520 the expandable which causes the vertical shrinkage of the pre-valve component due to reducing the distance between the superior and inferior components. As the pre-valve component shrinks (or is compressed), the compliant sheet wraps around to assume the form of a functional valve. Thus, expansion of the expandable structures results in formation of the valve in situ.

As used in this disclosure, except where the context requires otherwise, the term "comprise" and variations of the term, such as "comprising," "comprises" and "comprised" are not intended to exclude other additives, components, integers or steps.

Also, it is noted that the embodiments are disclosed as a process that is depicted as a flowchart, a flow diagram, a structure diagram, or a block diagram. Although a flowchart may disclose various steps of the operations as a sequential process, many of the operations can be performed in parallel or concurrently. The steps shown are not intended to be limiting nor are they intended to indicate that each step depicted is essential to the method, but instead are exemplary steps only.

In the foregoing specification, the invention has been described with reference to specific embodiments thereof. It will, however, be evident that various modifications and changes may be made thereto without departing from the broader spirit and scope of the invention. The specification and drawing are, accordingly, to be regarded in an illustrative rather than a restrictive sense. It should be appreciated that the present invention should not be construed as limited by such embodiments.

From the foregoing description, it will be apparent that the present invention has a number of advantages, some of which have been described herein, and others of which are inherent in the embodiments of the invention described or claimed herein. Also, it will be understood that modifications can be made to the device, apparatus and method described herein without departing from the teachings of subject matter described herein. As such, the invention is not to be limited to the described embodiments except as required by the appended claims.

Further description of the monolithic in situ forming valve system and its method of delivery can be found in Appendix A, which is incorporated by reference as though fully set forth herein. Appendix A is the content of a provisional application to which this application claims priority.

What is claimed is:

1. A monolithic in situ forming valve, comprising:
    a superior expandable structure;
    an inferior expandable structure; and
    a helical pre-valve component, the helical pre-valve component comprising:
        a first end attached with the superior expandable structure; and
        a second end attached with the inferior expandable structure, where the helical pre-valve component is formed such that expansion of the superior expandable structure and the inferior expandable structure causes the helical pre-valve component to transform from a non-functional valve into a functional valve held between each of the expandable structures;
    wherein the helical pre-valve component further includes a compliant sheet and at least two appendices; and
    wherein the expansion of the superior expandable structure and inferior expandable structure causes vertical shrinkage of the pre-valve component, which causes a first appendix to engage with the inferior expandable structure and a second appendix to engage with the superior expandable structure, thus inducing the compliant sheet to recoil to form the functional valve there between.

2. The apparatus of claim 1, wherein the appendices are formed of a shape memory material and form a hook-shape when exposed to a desired temperature.

3. The apparatus of claim 1, wherein appendices are configured to secure the pre-valve component to either the superior expandable structure or the inferior expandable structure, thereby fixedly securing the compliant sheet between the superior expandable structure and the inferior expandable structure.

4. The apparatus of claim 1, wherein the compliant sheet is integrated with a plurality of leaflets made of polymeric materials.

5. The apparatus of claim 1, wherein the compliant sheet is formed of a tissue selected from a group consisting of bovine tissue, porcine tissue, and equine pericardial tissue.

6. The apparatus of claim 1, wherein the superior expandable structure and inferior expandable structure are at least partially composed of a shape memory material, such that the superior expandable structure and inferior expandable structure have a first compressed memory state shape and second expanded memory state shape, where the superior expandable structure and inferior expandable structure are deliverable in a compressed state and upon expansion, are maintained in the second expanded memory state shape.

7. The apparatus of claim 1, wherein the superior expandable structure and the inferior expandable structure are in the form of a stent-like crown; and
    wherein the superior expandable structure and inferior expandable structure are at least partially composed of a magnetic material.

8. The apparatus of claim 1, further comprising a delivery apparatus connected with at least one of the superior expandable structure and the inferior expandable structure.

9. The apparatus of claim 8, wherein the delivery apparatus further comprises an expansion mechanism configured to selectively expand the superior expandable structure appended over the delivery apparatus and the inferior expandable structure appended over the delivery apparatus.

10. The apparatus of claim 9, wherein the expansion mechanism of the delivery apparatus is a balloon.

11. The apparatus of claim 1,
    wherein the appendices are formed of a shape memory material and form a hook-shape when exposed to a desired temperature;
    wherein appendices are configured to secure the pre-valve component to either the superior expandable structure or the inferior expandable structure, thereby fixedly securing the compliant sheet between the superior expandable structure and the inferior expandable structure;
    wherein the superior expandable structure and inferior expandable structure are at least partially composed of a shape memory material, such that the superior expandable structure and inferior expandable structure have a first compressed memory state shape and second expanded memory state shape, where the superior expandable structure and inferior expandable structure are deliverable in a compressed state and upon expansion, are maintained in the second expanded memory state shape;
    wherein the superior expandable structure and the inferior expandable structure are in the form of a stent-like crown;
    further comprising a delivery apparatus connected with at least one of the superior expandable structure and the inferior expandable structure; and
    wherein the delivery apparatus further comprises an expansion mechanism configured to selectively expand the superior expandable structure appended over the delivery apparatus and the inferior expandable structure appended over the delivery apparatus.

* * * * *